US008657830B2

(12) United States Patent
Sarin et al.

(10) Patent No.: US 8,657,830 B2
(45) Date of Patent: Feb. 25, 2014

(54) PELVIC PLANE LOCATOR AND PATIENT POSITIONER

(75) Inventors: Vineet Kumar Sarin, Thousand Oaks, CA (US); Robert A. Bruce, Ventura, CA (US); William Ralph Pratt, Newbury Park, CA (US); Clyde Ronald Pratt, Somis, CA (US)

(73) Assignee: Kinamed, Inc., Camarillo, CA (US)

( * ) Notice: Subject to any disclaimer, the term of this patent is extended or adjusted under 35 U.S.C. 154(b) by 57 days.

(21) Appl. No.: 12/878,594

(22) Filed: Sep. 9, 2010

(65) Prior Publication Data

US 2011/0009778 A1 Jan. 13, 2011

Related U.S. Application Data

(62) Division of application No. 10/815,369, filed on Apr. 1, 2004, now abandoned.

(60) Provisional application No. 60/459,695, filed on Apr. 2, 2003.

(51) Int. Cl.
*A61B 5/103* (2006.01)
*A61B 5/117* (2006.01)
*A61B 17/58* (2006.01)
*A61B 17/60* (2006.01)
*A61B 19/00* (2006.01)

(52) U.S. Cl.
USPC ............ 606/91; 606/102; 606/130; 600/587; 600/594; 600/426

(58) Field of Classification Search
USPC ............ 5/624, 621, 630, 648; 600/426, 587, 600/594; 606/53, 91, 102, 130
See application file for complete search history.

(56) References Cited

U.S. PATENT DOCUMENTS

| | | | |
|---|---|---|---|
| 5,141,512 A * | 8/1992 | Farmer et al. ................. | 606/87 |
| 6,205,411 B1 | 3/2001 | DiGioia, III et al. ........... | 703/11 |
| 6,311,349 B1 | 11/2001 | Kazakia et al. ................ | 5/624 |
| 6,711,431 B2 | 3/2004 | Pratt et al. .................... | 600/426 |
| 7,419,492 B2 * | 9/2008 | Yoon et al. .................... | 606/91 |
| 8,267,938 B2 * | 9/2012 | Murphy ......................... | 606/91 |
| 2004/0102792 A1 | 5/2004 | Sarin et al. | |
| 2008/0221570 A1 | 9/2008 | Sarin et al. | |

FOREIGN PATENT DOCUMENTS

| WO | WO 0121084 A1 | 3/2001 |
|---|---|---|
| WO | WO 02062248 A1 | 8/2002 |
| WO | WO 03073951 A | 12/2003 |

OTHER PUBLICATIONS

Office Action From U.S. Appl. No. 10/815,369, Dated: Mar. 10, 2010.
Supplementary European Search Report From European Patent Application No. 04758710.0, Dated: Apr. 7, 2010.
Lewinnek, George E., "Dislocations After Total Hip-Replacement Arthroplasties", Journal of Bone and Joint Surgery, vol. 60A, No. 2, pp. 217-220.

* cited by examiner

*Primary Examiner* — Max Hindenburg
*Assistant Examiner* — John Pani
(74) *Attorney, Agent, or Firm* — Koppel, Patrick Heybl & Philpott

(57) ABSTRACT

The invention includes both a method for acquiring the position of a patient's anterior pelvic plane, and a patient positioner or holder (apparatus) for securing a patient and acquiring the position of the patient's anterior pelvic plane. The method and apparatus facilitate definition of the anterior pelvic plane (APP) in the context of computer assisted hip surgery.

7 Claims, 3 Drawing Sheets

PELVIC PLANE LOCATOR AND PATIENT POSITIONER

RELATED APPLICATIONS

This application is a divisional of application Ser. No. 10/815,369 to Sarin et al., filed Apr. 1, 2004 now abandoned, which claimed priority to provisional application 60/459,695 filed on Apr. 2, 2003.

BACKGROUND OF THE INVENTION

1. Field of the Invention

This invention relates to orthopedic surgery generally and more specifically to computer assisted hip surgery.

2. Description of the Related Art

Total hip replacement or arthroplasty operations have become increasingly common in the United States, with more than 300,000 such operations occurring annually. Many of the procedures will eventually require revision, due to one of any number of problems. Problems can arise with the implant, which can wear, degrade or even fracture. In other cases, dislocation of the replaced hip can occur, causing extreme pain (not to mention inconvenience and expense). The incidence of dislocation has remained at approximately 2-6 percent, in spite of improvements to technique and materials.

It is known that the incidence of post-surgical dislocation is related to the orientation of the hip replacement components, particularly to the angular orientation of the acetabular shell component in relation to the bony anatomy. See Lewinnek et al., "Dislocation after total hip-replacement Arthroplasties," *Journal of Bone and Joint Surgery*, Vol. 60A, No. 2, PP. 217-220 (1978). The head and neck geometry of the implant is also thought to be a factor.

In spite of the published research, the typical surgeon has not adopted any sophisticated method of navigating hip replacement surgery, in spite of the availability of several techniques. The most prevalent method is to rely on an acetabular impactor tool with a handle placed at an angle predetermined so that if the handle is maintained at a level, horizontal orientation, the acetabular shell will be at a desired angle. This method fails to consider the considerable movement and variation in the patient's pelvic position during surgery; at worst it aligns the shell with the operating table (not necessarily the pelvis). More technological methods have been developed, including the sophisticated method described in U.S. Pat. No. 6,205,411 (and related applications) to DiGioia et al. (2001). The method of DiGioia is an advance over the prior methods (which he summarizes authoritatively in his "Background" section).

More recently, U.S. Pat. No. 6,711,431 to Sarin et al. (Mar. 23, 2004, assigned to Kinamed, Inc.) describes methods, apparatus and tools for image free, computer assisted navigation of hip surgery. The methods discussed in that application involve acquisition and tracking of a patient's pelvic plane by locating certain anatomical landmarks. The disclosed methods are less complex and expensive than reliance on radiological imagery. In connection with the methods disclosed by Sarin, it would be desirable to further facilitate reliable acquisition of the patient's pelvic plane.

SUMMARY OF TEE INVENTION

In view of the above problems, the present invention includes both a method for acquiring the position of a patient's anterior pelvic plane, and a patient positioner (apparatus) for securing a patient and acquiring the position of the patient's anterior pelvic plane.

The invention includes a method of determining the plane of a surgical patient's pelvis and inputting that plane into a computer via a tracking system, suitable for use in navigating partial or total hip replacement surgery, comprising the steps of: aligning the patient in relation to a patient positioning frame with pelvic anatomical features of the patient disposed in secure mechanical relationship with corresponding patient-engaging features on the positioning frame; acquiring with a tracking system the positions of a plurality of index points, the index points constrained to lie in a predetermined relationship with an anterior pelvic plane (APP) defined by the patient-engaging features; and defining a pelvic plane by calculation based upon the acquired positions of the index points and the predetermined relationship between the APP and the index points.

The apparatus of the invention includes a patient positioning frame, adapted to adjustably mount in opposition to an adjustable backrest, and suitable for use in connection with computer assisted surgery for finding the orientation of a patient's pelvic plane. The frame comprises: at least one anterior superior iliac spine (ASIS) locating feature, adapted to engage in close relation to the patient's ASIS; and at least one pubic locating feature, adapted to engage in close relation to the patient's pubic symphysis, the ASIS and pubic locating features defining an anterior pelvic plane (APP). The pelvic locating frame further comprises a group of index features, the group constrained to maintain a predetermined rotational relationship to the anterior pelvic plane (APP) defined by the ASIS and pubic locating features.

These and other features, aspects, and advantages of the present invention will become better understood with reference to the following description and claims.

DETAILED DESCRIPTION OF THE INVENTION

The present invention preferably functions in the context of a computer assisted surgical navigation system, to which it is particularly well suited. An example of a suitable system is disclosed in U.S. Pat. No. 6,711,431.

Figure 1:
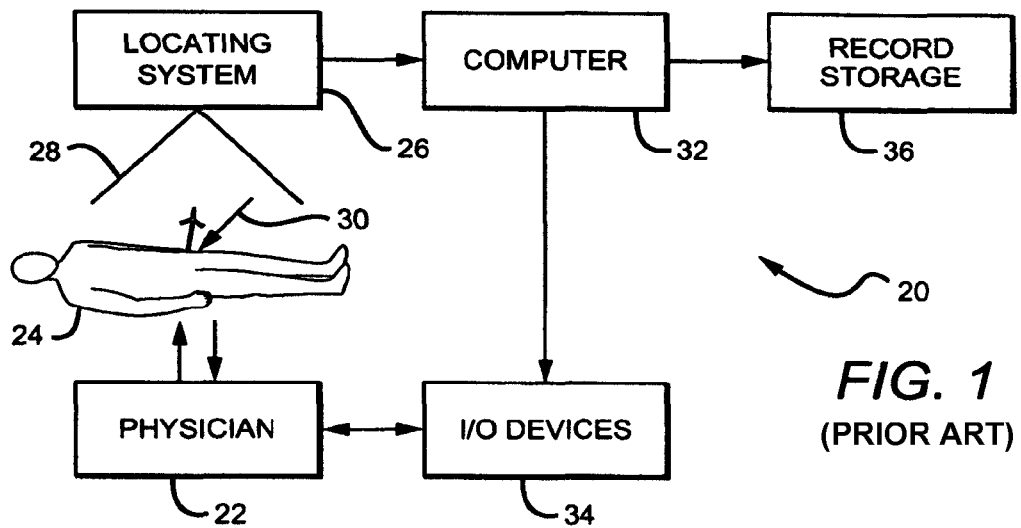
FIG. 1 is a block diagram showing a typical environment in which the invention is used, in connection with a computer-assisted hip surgery.

FIG. 1 shows a system-level block diagram of a prior art system or apparatus 20 which provides the preferred environment in which the present invention operates. The system or apparatus 20 is generally a computer aided system for navigating orthopedic surgery. A physician or other professional 22 performs a hip surgery (for example, total hip replacement) on a patient 24. An optical or equivalent locator or locating system 26 is disposed near the patient, so that the operating field is encompassed substantially within the field of view 28 of the locator 26. A suitable optical locator is available commercially, for example the "Polaris" available from Northern Digital Inc., in Waterloo, Ontario, Canada. Optical trackers or markers 30 are used during the operation. The markers 30 allow the locator 26 to acquire the positions and orientations of tools and anatomical reference points, as described below.

The optical locator 26 is interfaced with and outputs tracking data to a digital computer 32, which interprets the optical tracking data as it is received. Using well known geometric relationships, the computer is programmed to deduce from the optical field of view the actual positions and orientations of the markers, and, by extension, the positions and orientations of the instruments and/or anatomical features that are in known relationship to the markers. For example, suitable optical markers utilizing multiple reflective spheres are available from Traxtal Technologies in Toronto, Ontario, Canada. Markers with active light emitting devices such as LEDs are also available and could equivalently be used. Note that typical markers include three or more non-collinear components; this allows the locator and computer to determine not only the positions but the orientation (rotation) of such a marker in space. This capability is exploited in the methods described below.

Preferably, the computer 32 is also programmed with a user-friendly interface (software) which facilitates navigation. The physician or other personnel can view output (for example on a video monitor) and input instructions to the computer 32 via I/O devices 34, which suitably could include a monitor, keyboard, printer, foot pedals, and other input/output devices such as conventional "mouse" or similar pointing devices.

U.S. Pat. No. 6,711,431 (in FIG. 3 of that patent) also discloses a hand held probe which is trackable by the locating system, and which can be used to locate features by touching the feature with the tip of the probe, while cueing the computer 32 to acquire the probe position. Prior knowledge of the probe dimensions and geometry allows ready calculation of the position of said probe's tip. Other probes or locating tools could be used in addition to or instead of the disclosed probe.

Defining the Anterior Pelvic Plane

In total hip arthroplasty, the orientation of the acetabular implant is expressed in terms of two angular measurements: the abduction and version angles. These angles are defined relative to the anterior pelvic plane (APP) of the patient's body. Thus, in connection with hip arthroplasty it is very desirable to accurately and quickly define the APP. The APP is suitably defined by 3 anatomical landmarks on the pelvis: the two anterior superior iliac spines (ASIS's) and the pubic symphysis. In theory, the midpoint of the pubic tubercules defines the actual third point of the APP; in actual practice, this is usually assumed to be the pubic symphysis. A coordinate system based on the APP is defined and used to determine the abduction and version angles. The X-axis is defined by the line connecting the two ASIS points. The perpendicular line connecting the pubis symphysis to the X-axis defines the Y-axis, and the cross-product of the X and Y axes defines the Z-axis. Abduction is defined as rotation about the Z-axis and version is defined as rotation about the Y-axis.

Hip arthroplasty surgery is performed with the patient either resting supine (on their back) or held in the lateral decubitus position (on their side with surgery side facing up). For a patient resting in the supine position, the landmarks used to define the APP are relatively easy to identify and palpate during surgery. Patient soft tissue (i.e. pannus) and surgical draping do not in general prevent accurate palpation of the pelvic landmarks. An external holder is generally not used for patients resting in the supine position.

For the patient who is held in the lateral decubitus position, identification and palpation of the pelvic landmarks during surgery are made difficult by soft tissue, surgical draping, and the presence of an existing patient holder. The ispilateral (same side as surgery side) ASIS is usually easy to identify and palpate during surgery, but the contralateral ASIS (opposite to surgery side) and the pubic symphysis are difficult to identify and palpate accurately.

Figure 2:
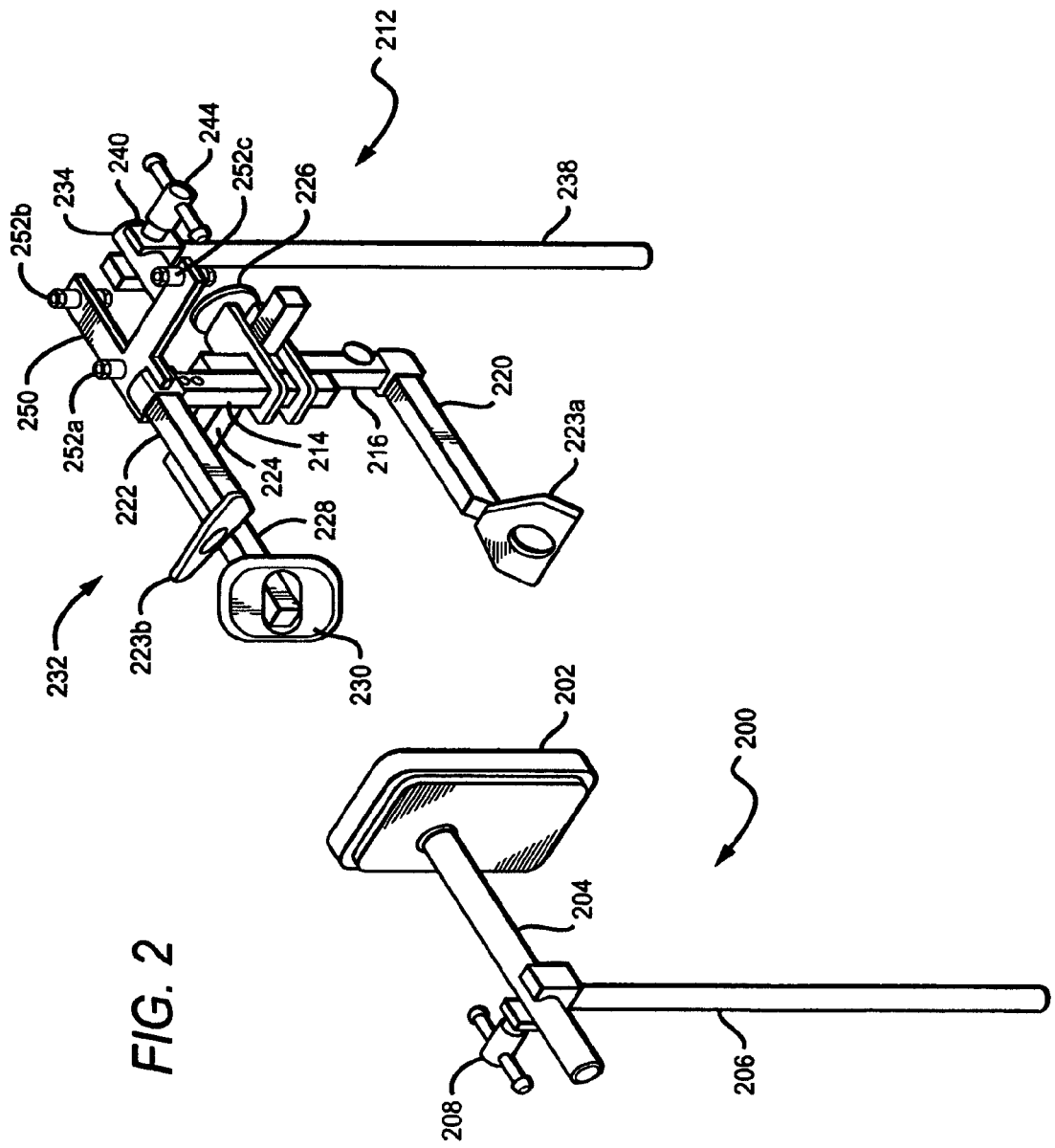
FIG. 2 is a perspective view, partially exploded, of the patient positioning frame in accordance with the invention.

FIG. 2 shows one embodiment of the invention. To hold the patient in the lateral decubitus position, the invention includes a back rest assembly 200. The assembly 200 includes an adjustable back rest 202 that adjusts by sliding to fit firmly against the back of a patient positioned in lateral decubitus position. The back rest, which could be conventional, is fixed to a horizontal adjustment rod 204 which in turn is slidably fixable to a vertical adjustment rod 206. The slidable adjustments of horizontal rod 204 are lockable by locking screw assembly 208. The entire assembly can be fixed to an operating table (not shown) by mounting vertical adjustment rod (preferably by slidably attaching to a rail, by means of a Clark socket, but other means could be used).

As is apparent from the figure, the vertical and horizontal adjustment rods are preferably cylindrical to allow rotational adjustment, to better engage the patient.

A pelvic locator assembly 212 is also shown in opposition to the back rest assembly 200, such that a patient can be disposed in between assemblies 200 and 212 and will be firmly clamped and secured. The pelvic locator assembly includes two vertical elongated members 214 and 216, which are slidably adjustable but lockable by tightening a pelvic width adjustment locking screw. Two horizontal, elongated members 220 and 222 are attached to the vertical members and extend horizontally toward the patient. (As used in this context, "horizontal" and "vertical" are intended in the reference frame of FIG. 2 only. If used with a supine patient, the directions would be interchanged.) At the end of the each horizontal member 220 and 222, there is an ASIS pad (223a and 223b) intended to press against and secure the patient by superficially engaging (two) ASIS. A pubic adjustment elongated member 224 is slidably mounted substantially perpendicularly to the members 214 and 216. Pubic adjustment member 224 is slidably mounted to allow adjustment for the pubic dimension of the patient. After adjustment the sliding member is lockable via a locking screw 226. A horizontal pubic extension member 228 is attached to pubic adjustment member and extends forward toward the patient, terminating in a pubis locator 230. Pubis locator 230 is provided to firmly engage the pubic symphysis but is preferably padded to prevent undue discomfort.

Elements 214 through 230 collectively define a support assembly 232. The entire support assembly is mounted on a horizontal adjustment rod 234. Locking screw 236, when tightened, locks the assembly to horizontal adjustment rod 234. When loosened, locking screw 236 allows rotational adjustment around the axis of rod 234.

The entire support assembly can be mounted to a vertical adjustment rod 238 by inserting horizontal rod 234 through a yoke 240 mounted on vertical adjustment rod. A slidable adjustment of horizontal rod 234 is lockable by locking screw assembly 244. Vertical adjustment rod 238 is attachable to an operating table (not shown).

As with the backrest assembly, the adjusting rods 238 and 234 are preferably cylindrical, to allow rotational adjustment about two axes (horizontal and vertical).

The support assembly can be detached from vertical adjustment rod 238 by loosening locking screw assembly 244, then removing horizontal adjustment rod 234 from yoke 240. This ability to remove the support assembly facilitates adjustment of the locator to a patient's pelvis, as described below.

Figure 3:
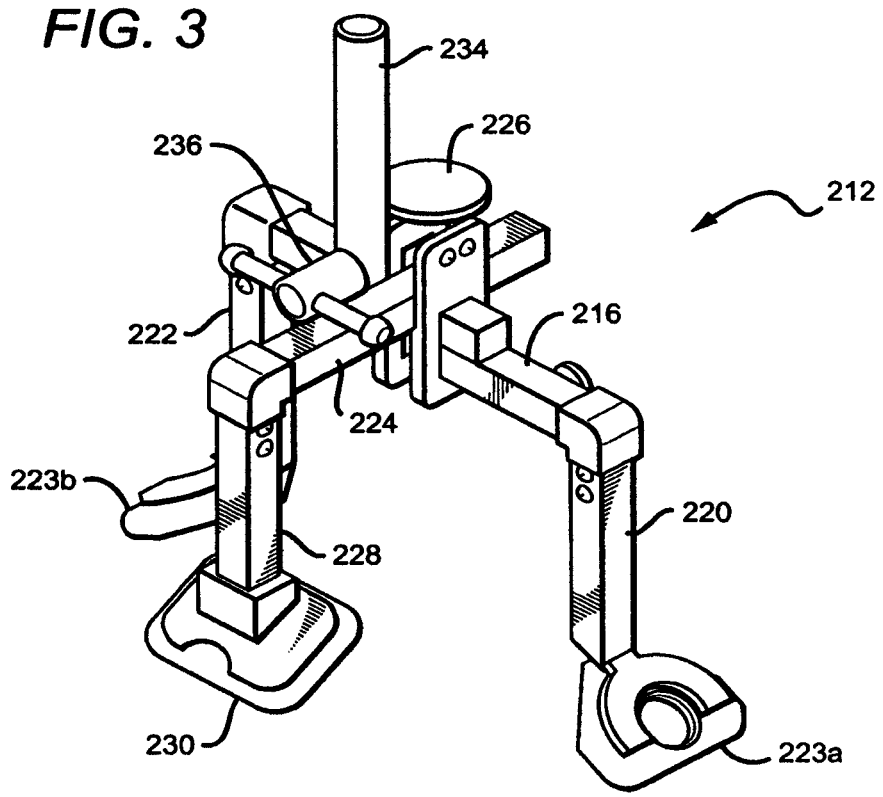
FIG. 3 is another perspective view of the pelvic locating portion of the patient positioning frame, rotated by 90 degrees from the position shown in FIG. 2.

The support assembly is shown in FIG. 3 as it appears when detached from vertical adjustment rod 238.

Referring back to FIG. 2, a "touch-plate" 250 is shown with 3 touch points 252a 252b and 252c used to define a local coordinate system. The touch plate 250 is (preferably removably) fixed to the support assembly in a way that maintains the predetermined angular relationship between the touch plate and the pubis and ASIS locators (223a, 223b and 230).

Figure 4:
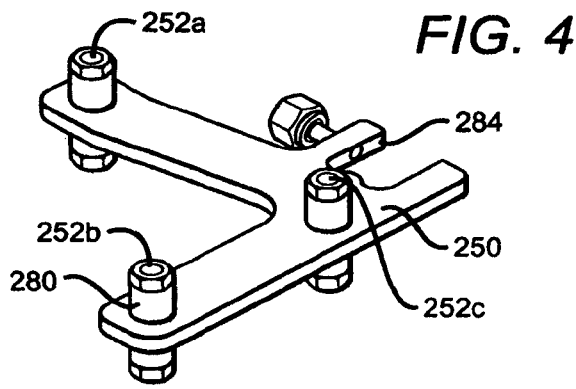
FIG. 4 is an enlarged perspective view of a touchplate component of the patient positioning frame of FIGS. 2 and 3, showing index features.

FIG. 4 shows the touch plate more closely. The three touch points 252a-252c ("index features") are defined by features in elevated posts 280. Preferably, the index features are formed or machined to engage a known pointer of a trackable probe, for example as shown in FIG. 3 of U.S. Pat. No. 6,711,431. The index features are mounted on a rigid plate 250, which is mountable to the support assembly by engaging the notch 284 with a (preferably square) member (214 in FIG. 2). A lock screw preferably secures the plate. Other means of mounting could be employed.

Note that the relationship between the touch plate assembly and the support pelvic and pubic locators is well defined and remains predictable, despite any adjustments of the pelvic locators and pubic locator. To elaborate further: a coordinate system defined by the index features is in a predetermined, known rotational relationship to the Anterior pelvic plane (APP) as defined by the ASIS locators (223a and 223b) and the pubic symphysis locator 230. In some embodiments, however, it is permissible to allow an arbitrary translation of the origin of the index feature coordinate system, so long as the system does not rotate in relation to the APP. The touch-plate of FIG. 4 constrains the touchplate to rotate in concert with the APP, because of the way in which the touchplate slot engages a rectangular support member. Other embodiments are possible, including some in which the touchplate is further constrained to remain fixed in translational as well as rotational relationship; for most applications, it is sufficient to constrain the rotational relationship to maintain a known predetermined relationship. More complex linkages could also be employed to constrain the index points to move in a predictable, predetermined relationship with the APP. Such variations are also within the scope of the invention.

The local coordinate system of the touch-plate defines the APP coordinate system by a predetermined known transformation. Thus, a vector is defined in the local coordinate system of the touch-plate that defines the orientation of a plane containing the ASIS locators and the Pubic symphysis locator. Through all degrees of freedom of the pelvic locator assembly, the touch-plate retains a known rotational relationship with the pelvic plane (as defined by the ASIS locators and the pubic locator).

It should be noted that the touch-points are not required to be touch-points exactly as shown in FIG. 4, but rather could be any markers/features with a predetermined known relationship to the point in question, like 3 LEDs etc. In one embodiment, the index features are emphasized by indentations in the posts 280, such indentations adapted to engage a complementary probe tip on a trackable probe. However, other index features could be used, such as protrusions, marks, posts, or other landmarks.

Method of Locating Pelvic Plane

The positions of the three touch points define the orientation of a coordinate system fixed in relation to the touch plate of FIG. 4. The local coordinate system of the touch-plate in turn defines the anterior pelvic plane (APP) because the ASIS finders and the pubis finder are located in a fixed known position relative to the local coordinate axes of the touch plate. The ASIS finders may adjust along the X-axis and the pubis symphysis locator may adjust along the Y-axis, but the APP coordinate system is not rotated by this adjustment. Thus, the local coordinate system of the touch-plate defines the APP coordinate system by a predetermined known transformation.

Figure 5:
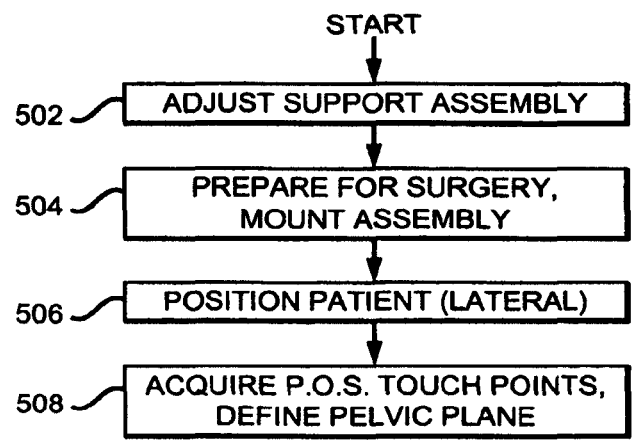
FIG. 5 is a flow diagram showing steps in a method in accordance with the invention.

Keeping this relationship in mind, the method of finding the APP using the apparatus of the invention is shown in FIG. 5.

First, in step 502 the support assembly 212 is adjusted to fit a patient's pelvic locators. Specifically, a doctor adjusts the two ASIS locators in preferably percutaneous but secure, close engagement with the left and right ASIS of the patient. He then adjusts the support assembly to engage the pubic symphysis with the pubic locator 230. This step can be performed while the patient is supine, and in one embodiment of the invention is specifically performed with the patient in a supine position. This step can be performed pre-operatively even during a preliminary office visit.

The invention is well adapted to fix the patient with percutaneous engagement of the ASIS and pubic locators. However, the apparatus and method could be modified to use penetrating locators such as needles. Percutaneous engagement is preferred in most embodiments for ease, simplicity, and to reduce injury to the patient.

Next, in step 504 after the patient is prepared for surgery, the support assembly 212 is mounted to an operating table.

Next, in step 506 the patient is positioned in the lateral decubitus (sideways) position in proximity to the support assembly, on the operating table. The back support assembly is then added, sandwiching the patient between the back support and the support assembly with the ASIS and Pubis properly engaged in the support assembly. Note that the support assembly and the back support can be adjusted by sliding and rotating the adjustment rods (horizontal and vertical) to accommodate the patient with minimal sliding of the patient on the operating table.

Next, in step 508 a locating system such as an optical locating system is used to acquire the positions of the three touch points on the touch plate. Preferably an optical tracking system and a touch probe are used, as described in U.S. Pat. No. 6,711,431.

Figure 6:
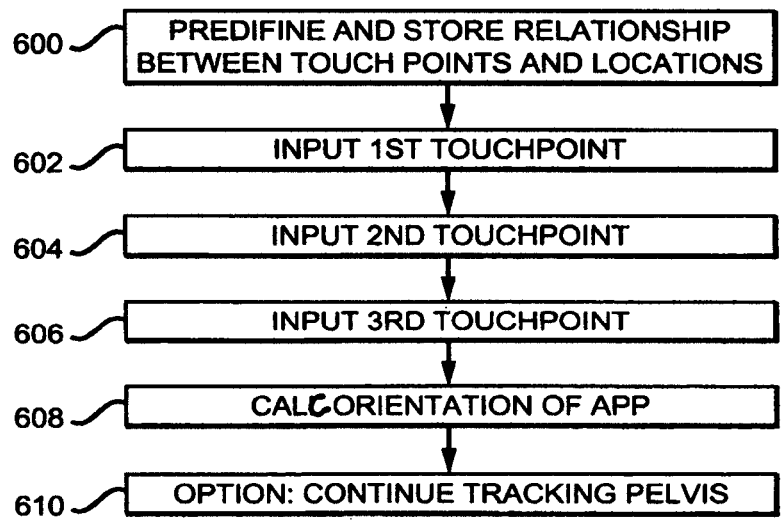
FIG. 6 is another flow diagram showing more detailed steps suitably used to define the pelvic plane in the method shown in FIG. 5.

FIG. 6 shows more detailed steps for acquiring the pelvic plane using the touch plate and an (optical) locating assembly. First, in step 600 a geometric relationship is predefined between the touch points and the ASIS and pubic locators. Note that the support system maintains the relative orientation of the touch plate vis a vis the pelvic locators, notwithstanding any adjustment of the locators. Thus, the three touchpoints of the touchplate define a coordinate system; the ASIS locators and the pubic locator define a plane (the APP); the orientation of the APP is defined in the touchplate coordinate system, reduced to a digitized mathematical set of parameters (modeled) and stored in a digital computer for later reference. Suitably, the orientation of the APP can be represented by a vector normal to the APP, or as two orthogonal vectors lying in the APP. The predetermined, stored relationship is relative.

The next steps are performed after the patient is engaged in the patient positioner, in lateral decubitis position on the operating table. In steps 602, 604, and 606 the positions of each touchpoints are input to the digital computer, suitably by touching each touchpoint with the manual probe while cueing the computer to acquire the position of the probe relative to the locating system (in an operating room coordinate system). The positions of each touchpoint are calculated (in three dimensions) by means described in U.S. Pat. No. 6,711,431 and the references cited therein. These positions are then used to calculate the real-time orientation of the touchplate assembly (relative to the tracking system, which defines an Operating Room reference frame).

Given the acquired orientation of the touchplate, the computer next calculates the orientation of the patient's APP (step 608). This is done by applying a transformation which compensates for the known (from step 600) relative relationship between the APP and the touchplate.

Optionally, but most preferably, the capabilities of the patient positioner are further exploited by placing a trackable target on the pelvis and continuing to track in real time the patient's pelvis (opt. Step 610). The dynamic tracking techniques which are used to further track the pelvis are described elsewhere, but in general rely on initial acquisition of the patient's APP. The initial location of the patient's APP can easily be acquired by use of the present invention as described above. Subsequently, a pelvic tracker can optionally be attached, for example by mounting a trackable target by bone screw to a patient's pelvis at an arbitrary angle. The arbitrary angle between the trackable target and the APP is then calculated and used to calculate a transformation. Once calculated, the patient can be released from the positioner (during surgery) and the APP can be tracked in real time by the pelvic tracker. In most cases, however, a surgeon may prefer to retain the patient secured in the position throughout surgery, to maintain stability.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A pelvic locating frame, adapted to adjustably mount in opposition to an adjustable backrest, and suitable for use in connection with computer assisted surgery for finding the orientation of a patient's pelvic plane, comprising:

a support assembly, comprising:
   at least two anterior superior iliac spine (ASIS) locating features, adapted to press against and superficially engage the patient's ASIS;
   at least one pubic locating feature, adapted to engage the patient's pubic symphysis, said ASIS and pubic locating features defining an anterior pelvic plane (APP);
   a group of index features, said group constrained to maintain a predetermined rotational relationship to said anterior pelvic plane (APP) defined by said ASIS and pubic locating features; and
   a plurality of elongated members to which said at least two ASIS locating features, said at least one pubic locating feature, and said group of index features are mounted;

a horizontal adjustment rod distinct from said support assembly to which said support assembly is mounted, said horizontal adjustment rod having an associated first axis along its length; and a vertical adjustment rod distinct from said support assembly to which said horizontal adjustment rod is mounted, said vertical adjustment rod being substantially perpendicular to said horizontal adjustment rod and having an associated second axis along its length, said elongated members arranged such that each can move independently of said vertical adjustment rod, said horizontal and vertical adjustment rods arranged such that said support assembly is capable of being rotated about said first and second axes, said pelvic locating frame arranged such that the position of said second axis does not move when said support assembly is rotated about said first axis, and does not move when said support assembly is rotated about said second axis.

2. The pelvic locating frame of claim 1, wherein said support assembly is adapted to allow engagement with two ASIS substantially vertically disposed, to accept a patient in a lateral decubitus position.

3. The pelvic locating frame of claim 1, wherein said group of index features comprises a non-collinear set of at least three features, said set defining a coordinate system in predetermined rotational relationship with said APP.

4. The pelvic locating frame of claim 3, wherein at least one of said index features comprises an indentation adapted to receive a complementary probe tip on a trackable probe.

5. The pelvic locating frame of claim 3, wherein said index features are constrained to move in a predetermined, coordinated relationship with said APP, so that the orientation of the APP can be calculated from known positions of the index features.

6. The pelvic locating frame of claim 5, wherein said index features are carried on a rigid plate;
   and wherein said rigid plate is attachable to said pelvic locating frame by an apparatus which constrains the plate to rotate in concert with said pelvic locating frame, locking the coordinate system of the index features to the APP.

7. The pelvic locating frame of claim 1, further comprising a back rest assembly arranged such that said patient can be held in the lateral decubitus position between said support assembly and said back rest assembly.

* * * * *